United States Patent
Chang

(10) Patent No.: US 8,369,924 B1
(45) Date of Patent: Feb. 5, 2013

(54) ECG LEADS SYSTEM FOR NEWBORN ECG SCREENING

(75) Inventor: Ruey-Kang Chang, Culver City, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 1014 days.

(21) Appl. No.: 11/951,083

(22) Filed: Dec. 5, 2007

Related U.S. Application Data

(60) Provisional application No. 60/882,122, filed on Dec. 27, 2006.

(51) Int. Cl.
  *A61B 5/0408* (2006.01)
(52) U.S. Cl. ........ 600/386; 600/391; 600/392; 600/393; 600/509
(58) Field of Classification Search .................. 600/382, 600/386, 388–393
  See application file for complete search history.

(56) References Cited

U.S. PATENT DOCUMENTS

| | | | |
|---|---|---|---|
| 3,888,240 A * | 6/1975 | Reinhold et al. | 600/390 |
| 4,233,987 A | 11/1980 | Feingold | |
| 4,498,480 A | 2/1985 | Mortensen | |
| 4,608,987 A | 9/1986 | Mills | |
| 4,957,109 A | 9/1990 | Groeger et al. | |
| 5,184,620 A | 2/1993 | Cudahy et al. | |
| 5,224,479 A | 7/1993 | Sekine | |
| 5,307,818 A * | 5/1994 | Segalowitz | 600/509 |
| 5,341,806 A * | 8/1994 | Gadsby et al. | 600/393 |
| 5,445,149 A | 8/1995 | Rotolo et al. | |
| 5,782,238 A | 7/1998 | Beitler | |
| 5,813,979 A * | 9/1998 | Wolfer | 600/373 |
| 5,865,736 A | 2/1999 | Baker et al. | |
| 5,868,671 A | 2/1999 | Mahoney | |
| 6,128,521 A * | 10/2000 | Marro et al. | 600/383 |
| 6,295,463 B1 | 9/2001 | Stenzler | |
| 6,334,065 B1 | 12/2001 | Al-Ali et al. | |
| 6,341,229 B1 | 1/2002 | Akiva | |
| 6,415,169 B1 * | 7/2002 | Kornrumpf et al. | 600/382 |
| 6,453,186 B1 | 9/2002 | Lovejoy et al. | |

(Continued)

FOREIGN PATENT DOCUMENTS

| | | | |
|---|---|---|---|
| GB | 2149918 | * | 6/1985 |
| WO | WO-99/40844 | | 8/1999 |

(Continued)

OTHER PUBLICATIONS

Ackerman, M.J., et al., "Postmortem Molecular Analysis of SCN5A Defects in Sudden Infant Death Syndrome", JAMA, vol. 286, No. 18 (Nov. 14, 2001) pp. 2264-2269.

(Continued)

*Primary Examiner* — Lee S Cohen
(74) *Attorney, Agent, or Firm* — Blakely Sokoloff Taylor & Zafman LLP

(57) ABSTRACT

An apparatus including a chest strip including a plurality of precordial leads positioned to correspond with desired lead placement for an electrocardiogram; and a plurality of limb leads coupled to the chest strip. A system including a chest strip including a plurality of precordial leads positioned to correspond with desired lead placement for an electrocardiogram; a plurality of limb leads coupled to the chest strip; and a transmitter coupled to plurality of precordial leads and the plurality of limb leads to transmit signals generated by the plurality of precordial leads and the plurality of limb leads. A method including coupling a chest strip including a precordial leads to a newborn; and generating an electrocardiogram from the precordial leads.

16 Claims, 4 Drawing Sheets

U.S. PATENT DOCUMENTS

| | | | |
|---|---|---|---|
| 6,611,705 B2 | 8/2003 | Hopman et al. | |
| 6,719,705 B2 | 4/2004 | Mills | |
| 6,847,836 B1 | 1/2005 | Sujdak | |
| 6,909,912 B2 | 6/2005 | Melker | |
| 7,444,177 B2 * | 10/2008 | Nazeri | 600/382 |
| 2002/0124295 A1 | 9/2002 | Fenwick et al. | |
| 2002/0133069 A1 | 9/2002 | Roberts | |
| 2003/0092996 A1 | 5/2003 | Lowe et al. | |
| 2006/0030782 A1 | 2/2006 | Shennib | |
| 2006/0047213 A1 | 3/2006 | Gavriely et al. | |
| 2006/0047215 A1 | 3/2006 | Newman et al. | |
| 2006/0069320 A1 | 3/2006 | Wolff et al. | |
| 2006/0149324 A1 | 7/2006 | Mann et al. | |
| 2006/0224072 A1 | 10/2006 | Shennib | |
| 2006/0247548 A1 | 11/2006 | Sarkar et al. | |
| 2006/0253007 A1 | 11/2006 | Cheng et al. | |
| 2006/0253044 A1 | 11/2006 | Zhang et al. | |
| 2007/0142715 A1 | 6/2007 | Banet et al. | |
| 2007/0276273 A1 * | 11/2007 | Watson, Jr | 600/511 |
| 2008/0177168 A1 * | 7/2008 | Callahan et al. | 600/382 |

FOREIGN PATENT DOCUMENTS

| | | |
|---|---|---|
| WO | WO-0193756 | 12/2001 |
| WO | WO-0222010 | 3/2002 |
| WO | WO-03011132 | 2/2003 |

OTHER PUBLICATIONS

Arnestad, M., et al., "Prevalence of Long-QT Syndrome Gene Variants in Sudden Infant Death Syndrome", Circulation, Issue 115 (Jan. 8, 2007) pp. 361-367.

Barclay, MD, L., "Some Cardiologists Recommend Routine ECG Screening of Newborns", Medscape Medical News, retrieved via Internet: <http://www.medscape.com/viewarticle/540941> (Jul. 14, 2006) 3 pp.

Quaglini, S., et al., "Cost-effectiveness of neonatal ECG screening for the long QT syndrome", European Heart Journal, vol. 27, (2006), pp. 1824-1832.

Schwartz, MD, P. J., "Newborn ECG Screening to Prevent Sudden Cardiac Death", Hearth Rhythm, vol. 3, Issue 11, retrieved via Internet: <http://sciencedirect.com> (Nov. 2006) 1353-1355.

Schwartz, MD, P.J., et al., "Prolongation of the QT Interval and the Sudden Infant Death Syndrome", The New England Journal of Medicine, vol. 338, No. 24 (Jun. 11, 1998) pp. 1709-1714.

Van Langen, I.M., et al., "Newborn screen to prevent sudden cardiac death?", Heart Rhythm, vol. 3, Issue 11 (Nov. 2006) pp. 1356-1359.

Wever, MD, E.F., et al., "Sudden Death in Patients Without Structural Heart Disease", Journal of the American College of Cardiology, vol. 43, No. 7 (Apr. 7, 2004) pp. 1137-1144.

Wilson, M., "ECG Screening for All Newborns Would Identify Life-Threatening Heart Condition", Medical News Today, retrieved via Internet: <http://medicalnewstoday.com/medicalnews> (Jul. 16, 2006) 2 pp.

Wilson, M., "Routine ECGs for newborns would identify life-threatening heart condition", Innovations Report, retrieved via Internet: <http://www.innovations-report.com> (Jul. 13, 2006) 3 pp.

LA BIOMED, Final office action dated Sep. 16, 2009 for U.S. Appl. No. 11/772,743.

"Los Angeles Biomedical Research Institute et al.", PCT International Search Report and Written Opinion mailed Nov. 11, 2007, PCT/US2007/015451, (Nov. 22, 2007).

Arlettaz, et al., "The contribution of pulse oximetry to the early detection of congenital heart disease in newborns", Eur J Pediatr, 165, (2006), 94-98.

Bakr, et al., "Combining pulse oximetry and clinical examination in screening for congenital heart disease", Pediatric Cardiology, 26, (2005), 832-835.

Geggel, "Conditions leading to pediatric cardiology consultation in a tertiary academic hospital", Pediatrics, 114:4, (2004), 409-17.

Hoke, et al., "Oxygen saturation as a screening test for critical congenital heart disease: a preliminary study", Pediatric Cardiology, 23, (2002), 403-409.

Knowles, et al., "Newborn screening for congenital heart defects: a systematic review and cost-effectiveness analysis", Health Technology Assessment, 9:44, (Nov. 2005).

Koppel, et al., "Effectiveness of pulse oximetry screening for congenital heart disease in asymptomatic newborns", Pediatrics, 111:3, (Mar. 2003), 451-455.

Li, et al., "Will a handheld ultrasound scanner be applicable for screening for heart abnormalities in newborns and children?", J Am Soc Echocardiogr., 16:10, (2003), 1007-14.

Reich, et al., "The use of pulse oximetry to detect congenital heart disease", J Pediatr, 142, (2003), 268-272.

Richmond, et al., "Routine pulse oximetry in the asymptomatic newborn", Arch Dis Child Fetal Neonatal Ed., 87, (2002), F83-8.

Rosati, et al., "Indications and limitations for a neonatal pulse oximetry screening of critical congenital heart disease", J. Perinat. Med., 33, (2005), 455-457.

Wren, et al., "Presentation of congenital heart disease in infancy: implications for routine examination", Arch Dis Child Fetal Neonatal Ed., 80, (1999), F49-53.

* cited by examiner

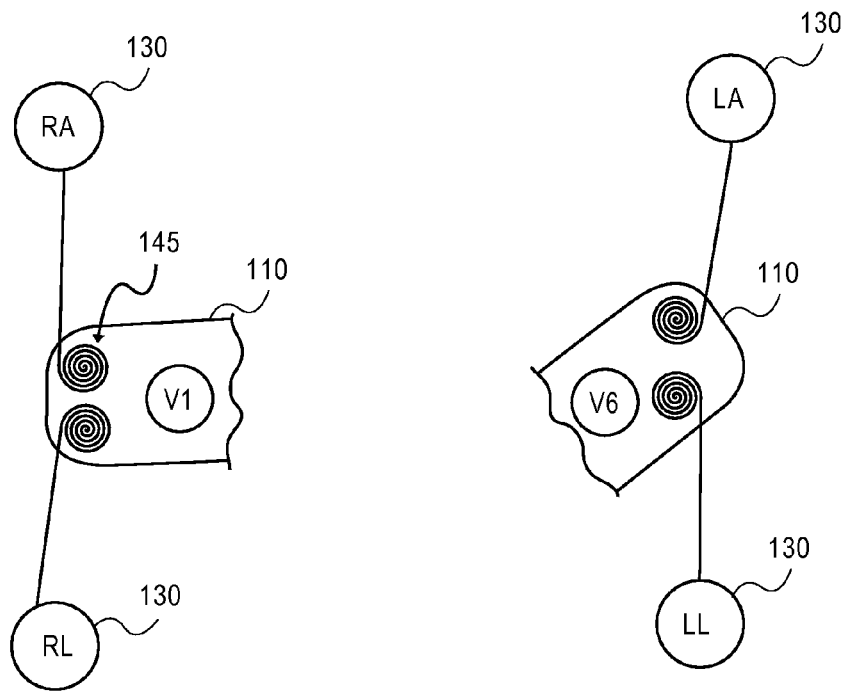
FIG. 3
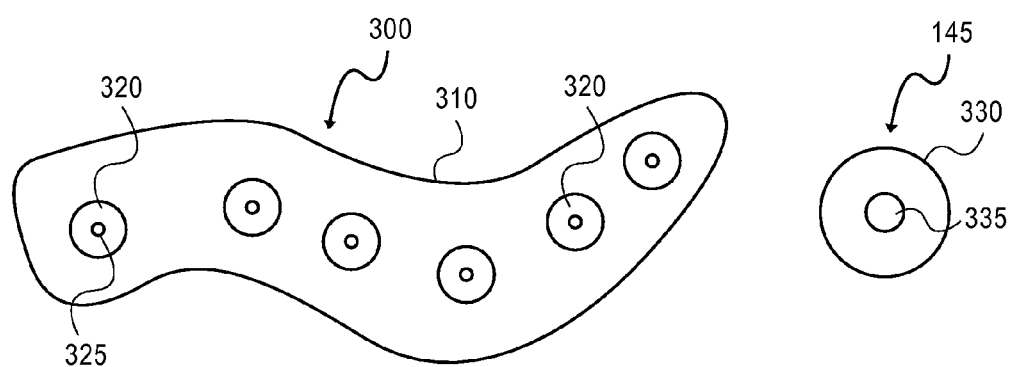
FIG. 4
FIG. 5

ECG LEADS SYSTEM FOR NEWBORN ECG SCREENING

CROSS-REFERENCE TO RELATED APPLICATION

This application claims the benefit of the earlier filing date of U.S. Provisional Patent Application No. 60/882,122, filed Dec. 27, 2006, and incorporated herein by reference.

BACKGROUND

1. Field

Neonatal electrocardiogram screening.

2. Background

Long QT syndrome (LQTS) is a genetic disease characterized by an abnormally prolonged QT interval in the electrocardiogram (ECG) waveform. LQTS is a leading cause of sudden cardiac death in the young. When infants with undiagnosed LQTS die, their sudden deaths are often labeled as sudden infant death syndrome (SIDS) because no apparent cause of death could be found by autopsy. Using post-mortem genetic analysis, researchers have found that more than 10% of SIDS cases are actually due to undiagnosed LQTS. LQTS can be diagnosed by a routine 12-lead ECG. Once diagnosed, the treatments for LQTS, including beta-blocker therapy and internal cardiac defibrillator (ICD), are very effective in preventing cardiac arrhythmia and sudden death. Therefore, some European countries are considering the possibility of introducing neonatal (days 15-25) ECG screening as part of their National Health Services. Among the European countries, Italian Ministry of Health funded an electrocardiogram (ECG) screening program on over 50,000 babies to assess the feasibility and outcomes of a nationwide neonatal ECG screening. The program has been tremendously successful, and such success has generated enthusiasm toward implementation of a nationwide screening program from many European nations and the United States.

Since the proposed screening ECGs are targeted at two to four weeks of life, the screenings for LQTS proposed will likely have to be done at a pediatrician's office. Most nurses or nurse's assistants are not trained to perform newborn ECGs. A regular ECG machine has 10 long cables which often tangle among themselves. When conducting an ECG test, the operator needs to place 10 electrodes (stickers) on the patient and match the cables with each respective electrode on the patient. This process of untangling the cables, placing electrodes, and matching the cables and electrodes takes skill and time.

Performing an ECG on a newborn is challenging and often takes up to 20 minutes or more. Placing the leads on a newborn is difficult because of limited space on the torso and the babies are not cooperative. Furthermore, performing an ECG on a newborn using the current complicated leads system by inexperienced nurses is prone to error, such as wrong leads placement, artifacts, and inadequate ECG signal acquisition.

To solve the issues with improper leads placement and tangling of cables, prior inventions have used pre-positioned leads or one-piece design. U.S. Pat. Nos. 4,608,987 and 5,224,479 describe a vest containing pre-positioned leads, which is cumbersome to use in babies and requires a large area of skin contact when worn. Chest strip designs have been proposed by U.S. Pat. Nos. 4,233,987, 5,184,620, and 5868671. The limitations of these designs are that they are not designed for use in newborns and infants; and only three to six chest leads are typically provided (e.g., the strips lack limb leads) and therefore cannot be used for QT analysis. U.S. Pat. No. 6,847,836 proposes a one-piece chest pad design for use of ECG monitoring in the emergency room. The chest pad design is not specific for newborns and infants, and has a large skin contact area, which is an important limitation for use in babies because of their sensitive skin. Furthermore, the limb lead positions in the chest pad design of U.S. Pat. No. 6,847,836 are not generally proper for accurate measurement of QT intervals on a 12-lead ECG. As a result, QT analysis using such a design and system is not generally accurate.

ECG is mostly performed in adults, especially elderly people. ECG on newborns used to be a rare practice. None of the current ECG machine or leads system is designed for use in newborns or infants. As many nations are considering implementing a nationwide newborn ECG screening program, there is an urgent need for a simple, quick and error-proof ECG leads system for newborns. The current design is an ECG leads system specifically designed for newborns to be used in pediatrician's office or hospital for newborn screening.

SUMMARY

An ECG leads system designed for performing newborn ECG is disclosed. In one embodiment, the leads system includes a chest strip which contains precordial leads; retractable limb leads, wireless connector or cable and a leads adapter. This system with simple, pre-positioned leads allows quick and accurate leads placement for conducting newborn ECG.

A method of performing an ECG using an ECG leads system is also disclosed. In one embodiment, the method may be used on a newborn infant to detect LQTS and minimize the risk for SIDS.

BRIEF DESCRIPTION OF THE DRAWINGS

FIG. 3 shows a schematic side view of two portions of the chest strip of the ECG leads system of FIG. 1 and shows retractable limb leads partially retracted.

FIG. 4 shows a schematic top view of a disposable electrode strip suitable for use with the chest strip of the ECG leads system of FIG. 1.

FIG. 5 shows a schematic top view of a disposable electrode lead suitable for use with limb leads of the ECG leads system of FIG. 1.

DETAILED DESCRIPTION

An ECG leads system for conduction of newborn ECG is described. In one embodiment, this ECG leads system connects directly with an ECG machine. In another embodiment, this ECG leads system includes an adapter that can connect to the cables of an ECG machine to allow the use with existing ECG machines already in hospitals or physician's offices.

Figure 1:
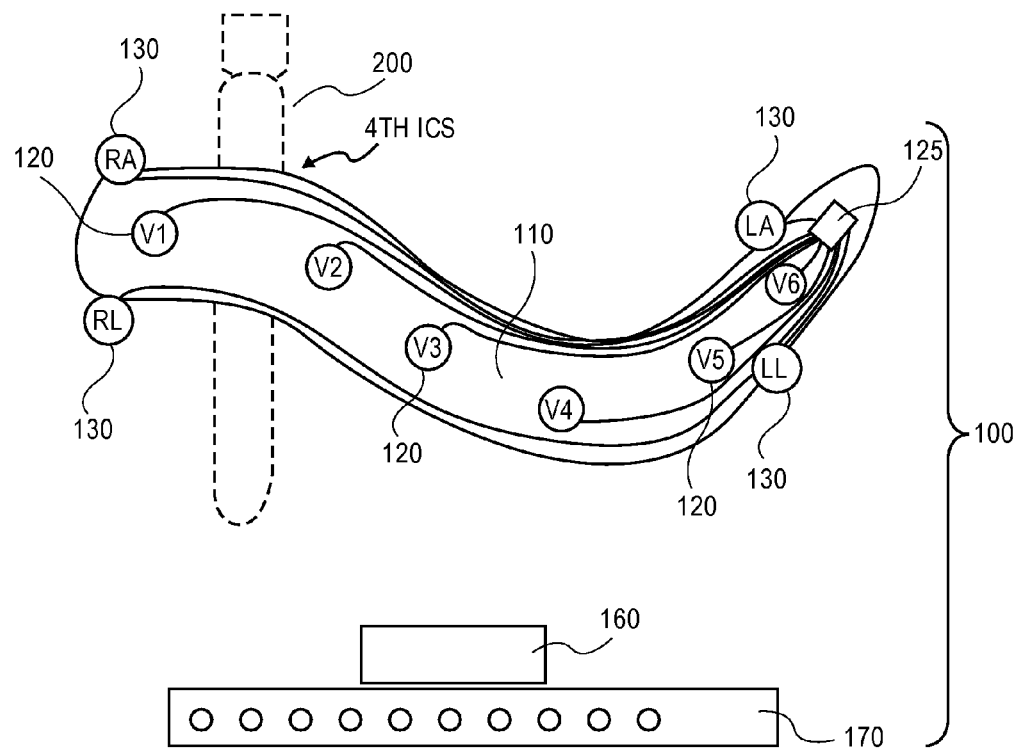
FIG. 1 illustrates a schematic view of an embodiment of an ECG leads system including a cross-sectional top view of a chest strip, and side views of a receiver and an adapter.

FIG. 1 illustrates an embodiment of an ECG system. In the illustrated embodiment, ECG system 100 includes the following components: chest strip 110 including a plurality of precordial leads 120 and transceiver 125; retractable limb leads 130; receiver 160; and adapter 170 to connect to an ECG machine. A cross-sectional top view of chest strip 110 is shown to illustrate precordial leads 120 and transceiver 125.

Figure 6:
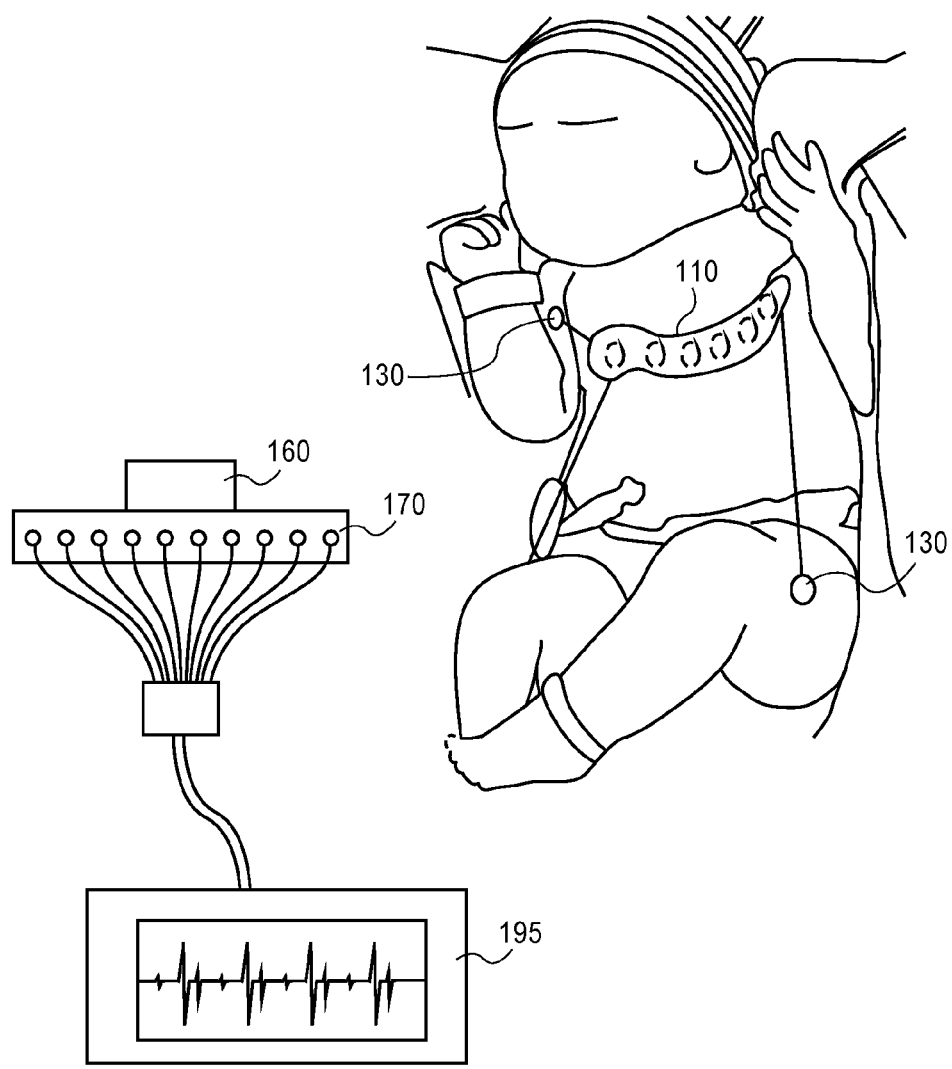
FIG. 6 shows a schematic view of the ECG leads system recording an ECG of a newborn.

In one embodiment, chest strip 110 is designed to embed six precordial leads 120 (V1, V2, V3, V4, V5, and V6). The chest strip is shaped in a way shown in FIG. 1 so that when placed on a newborn's chest, precordial leads 120 (V1 to V6) will be in proper positions for routine ECG leads placements. As shown in FIG. 1, the chest strip will be placed so that V1 will be in the $4^{th}$ intercostal space (ICS) on the right sternal border, and V2 will be in the $4^{th}$ ICS on the left sternal border. The $4^{th}$ ICS is at approximately the nipple line which is a convenient landmark for chest strip placement. Indicators for sternum position are shown on the chest strip to assist the operator to position V1 and V2 at opposite sides of the sternum. The positions of V3 to V6 will also be placed properly and chest strip 110 will be shaped accordingly. V4 will be at $5^{th}$ ICS in the left mid-clavicular line; V3 will be half way between V2 and V4; V5 will be at the level of V4 in the left anterior auxiliary line, and V6 will be at the level of V4 in the left mid-auxiliary line. Because the chest sizes of newborns at three to five kilograms (kg) body weight do not vary widely, chest strip 110 may be one size that will fit all. In one embodiment, the width of the chest strip is 2 cm and length is 12 cm. In another embodiment, the dimensions are reduced to fit premature infants or infants with smaller chest sizes. FIG. 6 shows chest strip 110 applied to the chest of a newborn.

Figure 2:
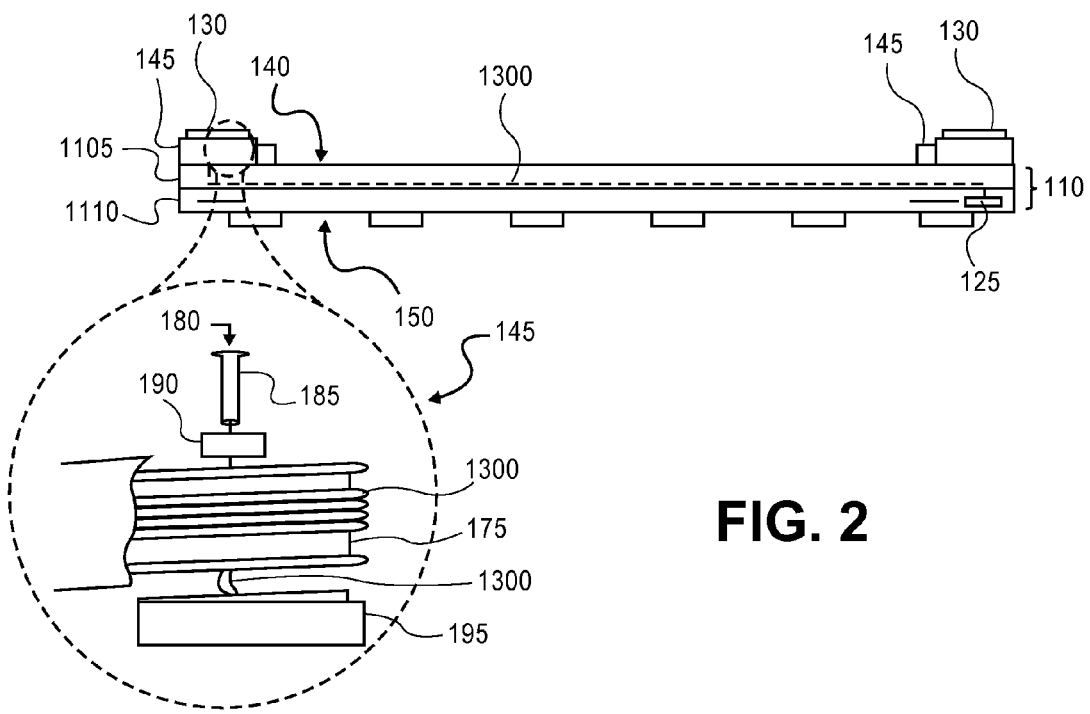
FIG. 2 shows a side view of the chest strip of FIG. 1.

In one embodiment, chest strip 110 is made of nonconductive, flexible material such as plastic, or natural or synthetic fabric. FIG. 2 shows a side view of an embodiment of chest strip 110. In this embodiment, chest strip 110 is made of two layers of material (material layer 1105 and material layer 1110). Chest strip 110 has surface 140 intended to face away from a newborn's skin when chest strip 110 is applied and surface 150 opposite surface 140 and having leads 150 exposed therethrough. Surface 140 of chest strip 110 is generally smooth with no exposed components. On opposite surface 150 of chest strip 110, six round shape precordial leads 120, each representatively 10 millimeters (mm) in diameter, are positioned in V1, V2, V3, V4, V5, and V6 locations. Precordial leads 120 are made of a conductive material such as silver. Each of the leads V1 to V6 connects to its own wire that connects to transceiver 125 or a cable (see FIG. 5 and the accompanying text). The wires are electrically insulated from one another so that there will be no interference among the leads. In the embodiment shown in FIG. 2, precordial leads 120 may be placed through layer 1110 with wires connected between the leads and transceiver 125. Layer 1105 lies on the wires and hides the wires in chest strip 110 (e.g., the wires are disposed between layer 1110 and layer 1105).

In one embodiment, ECG system 100 shown in FIG. 1 and FIG. 2 includes limb leads 130 connected to chest strip 110. Right limb leads 130, RA and RL, are located on the right end of chest strip 110 when the chest strip is applied to a newborn's chest (FIG. 1). Left limb leads 130, LA and LL, are located on the left end of chest strip 110 (FIG. 1). FIG. 6 shows limb leads 130 applied to a newborn In one embodiment, a wire extends between each limb lead 130 and transceiver 125, with a portion of each wire extending through chest strip 110 similar to the wires that connect the precordial leads 130 to transceiver 125. The wires are electrically insulated from one another and from the wires of precordial leads 120. As shown in FIG. 2, in one embodiment, the wires that connect limb leads 130 to transceiver 125 extend at each end from chest strip 110 into a respective hub 145 (shown illustratively on surface 140 of chest strip 110). Each hub 145 includes drum 175 on which, in this example, wire 1300 is wound. Drum 175 is rotatable on axis 180 defined by axle bolt or rivet 185 and bearing 190. Spring biased roller 195 is connected to wire 1300 interiorly of drum 175 and having a center axis co-axially aligned with axis 180, the roller functioning to exert a retract force continuously on wire 1300 even when the wire is uncoiled from drum 175 and hub 145. Wire 1300 is continuously biased toward a storage position in hub 145.

The wires connecting to limb leads 130 are self-retractable or are biased toward coiling the wires in respective hubs 145. A pulling force on a limb lead is required to uncoil a wire for a limb lead. Release of the pulling force returns the wire to a coiled configuration. In this manner, when not placed on a limb of a newborn, the leads are conveniently housed in respective hubs 145 to minimize wires tangling. When in use, after chest strip 110 is properly placed on the newborn, each of limb leads 130 can be pulled out to position in the proper places for the regular limb leads placement (FIG. 3 and FIG. 6). In one embodiment, the wires for upper limb leads (RA and LA) are five inches when fully uncoiled, and the wires for lower limb leads (RL and LL) are eight inches when fully uncoiled. The lengths of the limb leads wires will allow proper placement of limb leads 130. In one embodiment, a stop may be included on each wire when a lead is uncoiled and positioned. Such a stop may be as simple as a clip on the wire directly outside hub 145 or more elaborate such as an actuator connected to hub 145 to lock roller 195. When an ECG recording is finished, the operator will push the actuator to unlock roller 195 and allow a wire to retract back to hub 145 and return the lead into a stored position (FIG. 2).

Referring to precordial leads 120 and limb leads 130, in one embodiment, the leads are not placed directly on a newborn's skin. Instead, disposable electrodes are representatively used to ensure good skin contact and connection with the ECG leads. FIG. 4 shows a side view of disposable electrode 300 that is in a similar shape of chest strip 110 with six round-shaped ionically conductive hypoallergenic hydrogel adhesives 320 placed in similar positions of the V1, V2, V3, V4, V5 and V6 leads 120 on chest strip 110 (see FIG. 1). In one embodiment, each adhesive 320 is 16 millimeters (mm) in diameter, with electrically conductive button 325 (e.g., a stainless steel button) in the center on a first surface. A second surface of electrode 300 is covered by a removable plastic cover. Prior to applying chest strip 110 to a newborn's chest, an operator will place the disposable electrode 300 on the underside of chest strip 110 such that each button 325 in the center of each adhesive 320 is in proper contact with the electrically conductive (e.g., silver) center of leads 120 on the chest strip. Then the operator will remove the thin plastic cover of electrode 300 to expose an adhesive side of each adhesive 320 and apply electrode 300 and chest strip 110 on the newborn's chest. In one embodiment, the adhesive between electrode 300 and chest strip 110 is hypoallergenic hydrogel. In an embodiment where the adhesive is associated only with adhesive 320 rather than the entire chest strip, the contact with a newborn's skin is minimized.

FIG. 5 shows disposable electrode 305 that may be used with the limb leads 130. Electrode 305 includes round ionically conductive hypoallergenic hydrogel adhesive 330, 20 mm in diameter, with a conductive (e.g., stainless steel) button 335 in the center on one surface to contact a conductive portion of limb lead 130. A removable plastic cover may be placed over a second adhesive surface of adhesive 330. The cover will be removed prior to attaching the electrode on the newborn. In one embodiment, a hypoallergenic hydrogel is provided on the adhesive surface of each electrode 305 that will ensure good skin contact. After chest strip is placed properly on the chest, the operator will pull each individual limb leads out and clip or snap on a respective electrode 330.

As noted above, in one embodiment the wires from limb leads 130 (RA, RL, LA, LL) and precordial leads 120 (V1, V2, V3, V4, V5, V6) run through chest strip 110 individually and connect to transceiver 125. Transceiver 125 is, for example, a Bluetooth chip located at the left end of chest strip 110. In one embodiment, transceiver 125 is programmed to receive and transmit ECG signals from limb leads 130 and precordial leads 120. In the embodiment of ECG system 100 shown in FIG. 1, transceiver 125 wirelessly sends ECG signals received from the various leads to receiver 160, such as a Bluetooth chip. Receiver 160 then distributes the received signals to contact points of adapter 170 (contact points corresponding to signals for six precordial leads V1, V2, V3, V4, V5, V6, and four limb leads RA, RL, LA, LL). Such signals may be transmitted from adapter 170 by hard wiring a connection between the contact points and an ECG machine (see FIG. 6).

Adapter 170 is designed to make ECG leads system 100 compatible with existing, commercially available ECG machines. In one embodiment, the contact points on adapter 170 are the same as used on regular ECG electrodes, which allows the leads from commercial ECG machine to clip on or clamp on. FIG. 6 shows ECG system 100 connected to ECG machine 195 and illustrates an ECG signal displayed on ECG machine 195.

Figure 7:
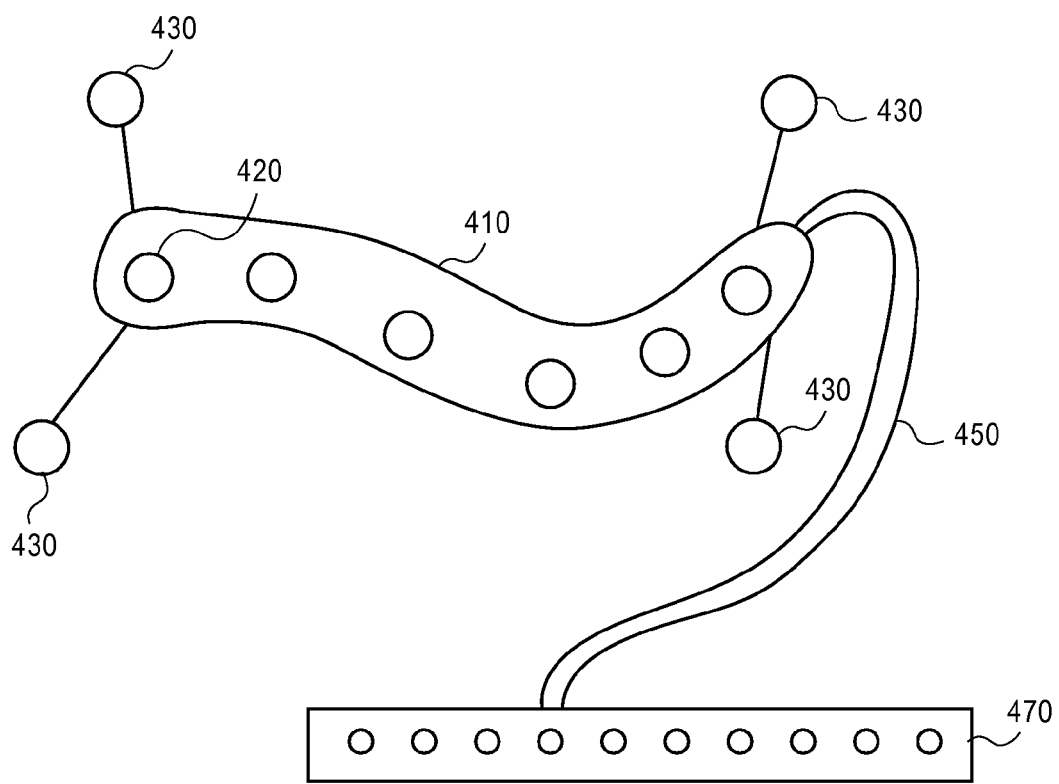
FIG. 7 shows a schematic side view of another embodiment of an ECG leads system including a chest strip, a cable, and an adapter.

FIG. 7 shows another embodiment of an ECG system where the connection between a chest strip and a leads adapter uses wired cable instead of wireless technology. FIG. 7 shows chest strip 410 including precordial leads 420 (V1, V2, V3, V4, V5, V6). FIG. 7 also shows limb leads 430 (RA, RL, LA, LL) connected by individual wires to chest strip 410. The wires for precordial leads 420 and limb leads 430 extend into harness 450 which connects to adapter 470. The signals at adapter 470 may then be transferred (e.g., via wires) to an ECG machine. Alternatively, harness 450 may connect limb leads 430 and precordial leads 420 on chest strip 410 directly to an ECG machine without the use of adapter 470. The wires inside harness 450 are electrically insulated from one another. A representative length of harness 450 is from one foot up to 12 feet depending on the needs.

The ECG system described herein has many advantages over traditional ECG leads and cables. In particular, the ECG system described herein has a simple design that is easy to use, relatively error-proof, and compatible with current ECG machines. The ECG system described herein also minimizes skin contact on newborn thereby decreasing the risk for infection and/or skin reaction.

In the preceding detailed description, the invention is described with reference to specific exemplary embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An apparatus comprising:
 a chest strip having dimensions suitable for a chest of a newborn, the chest strip comprising (1) an indicator for a placement of the chest strip on the chest of a newborn relative to a sternum of the newborn so that a V1 precordial lead will be in a 4th intercostal space on a right sternal border and V2 precordial lead will be in a 4th intercostal space on a left sternal border and (2) a plurality of precordial leads positioned to correspond with desired lead placement for an electrocardiogram; and
 a plurality of retractable limb leads including a right arm limb lead and a left arm limb lead coupled to the chest strip and extendable therefrom from an unextended configuration, wherein such limb leads are biased to retract and return to the unextended configuration.

2. The apparatus of claim 1, further comprising a plurality of wires ones of which are coupled to each limb lead and biased to retract to a coiled position as the unextended configuration.

3. The apparatus of claim 1, further comprising a plurality of wires ones of which are coupled to each of the precordial leads and a transceiver coupled to the plurality of wires.

4. The apparatus of claim 3, wherein the transceiver is configured to transmit wireless signals generated by the plurality of limb leads.

5. The apparatus of claim 1, wherein the chest strip is a first strip, the apparatus further comprising a second strip comprising a plurality of conductive adhesives positioned to align with the precordial leads of the chest strip.

6. The apparatus of claim 5, wherein each of the plurality of conductive adhesives comprises an electrically conductive button.

7. A system comprising:
 a chest strip having dimensions suitable for a chest of a newborn, the chest strip comprising (1) an indicator for a placement of the chest strip on the chest of a newborn relative to a sternum of the newborn and (2) a plurality of precordial leads positioned to correspond with desired lead placement for an electrocardiogram;
 a plurality of retractable limb leads including a right arm limb lead and a left arm limb lead coupled to the chest strip and extendable therefrom from an unextended configuration, wherein such limb leads are biased to retract and return to the unextended configuration; and
 a transmitter coupled to plurality of precordial leads and the plurality of limb leads to transmit signals generated by the plurality of precordial leads and the plurality of limb leads.

8. The system of claim 7, further comprising a receiver, wherein the transmitter is configured to wirelessly transmit signals to the receiver.

9. The system of claim 8, further comprising an adapter coupled to the receiver, the adapter configured to transmit the signals to an electrocardiogram machine.

10. The system of claim 7, wherein the transmitter comprises a plurality of wires ones of which are coupled to respective ones of the plurality of precordial leads and the plurality of limb leads.

11. The system of claim 7, further comprising a sacrificial chest strip comprising a plurality of electrodes aligned with the precordial leads of the chest strip.

12. The system of claim 7, further comprising a plurality of sacrificial limb strips each comprising an electrode.

13. A method comprising:
 coupling a chest strip having dimensions suitable for a chest of a newborn and comprising a plurality of precordial leads to a chest of a newborn using an indicator on the chest strip for a sternum position of the newborn so that a V1 precordial lead will be in a 4th intercostal space on a right sternal border and V2 precordial lead will be in a 4th intercostal space on a left sternal border;
 extending and coupling self retractable limb leads from an unextended position to each of the limbs of the newborn;

generating an electrocardiogram sufficient for screening for long QT syndrome from the precordial leads and the limb leads; and after generating an electrocardiogram, allowing the limb leads to return to the unextended position.

14. The method of claim 13, further comprising:

prior to coupling the chest strip to a newborn, coupling a disposable electrode to the chest strip, the disposable electrode comprising a plurality of conductive adhesives oriented with respective ones of the plurality of precordial leads of the chest strip.

15. The method of claim 14, wherein the disposable electrode has a similar shape to the shape of the chest strip.

16. The method of claim 13, further comprising:

prior to coupling the limb leads to the newborn, coupling disposable electrodes to the newborn, and coupling limb leads comprises coupling respective ones of the limb leads to respective ones of the disposable electrodes.

* * * * *